Figure 1:
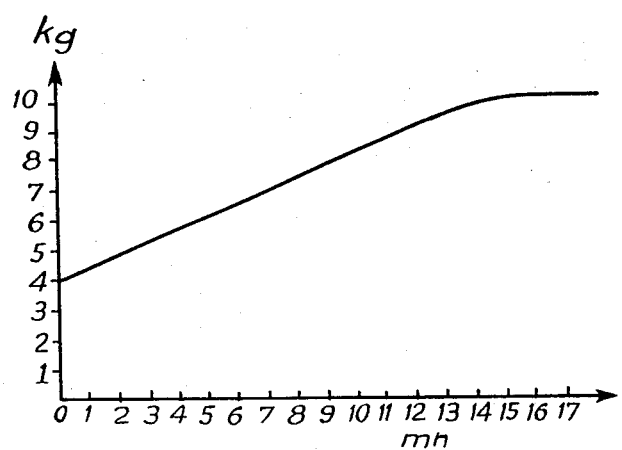

United States Patent [19]

Grouiller et al.

[11] Patent Number: 4,629,624

[45] Date of Patent: Dec. 16, 1986

[54] INERT MATRIX BASED ON POLYCAPROLACTONE FOR THE ORAL ADMINISTRATION OF A DRUG, AND METHOD FOR THE PREPARATION OF THE GALENIC FORM COMPRISING THIS MATRIX

[75] Inventors: Hervé Grouiller; Fabien Christ, both of Dijon, France

[73] Assignee: Laboratoire d'Hygiene et de Dietetique (L.H.D.), Paris, France

[21] Appl. No.: 686,214

[22] Filed: Dec. 26, 1984

[30] Foreign Application Priority Data

Jan. 2, 1984 [FR] France .............................. 84 00015

[51] Int. Cl.$^4$ .............................................. A61K 31/74
[52] U.S. Cl. ........................................ 424/78; 514/951
[58] Field of Search ................... 514/951; 424/16, 19, 424/21, 22, 32, 78

[56] References Cited

U.S. PATENT DOCUMENTS

| | | | |
|---|---|---|---|
| 3,773,919 | 11/1973 | Boswell et al. | 424/22 |
| 3,929,937 | 12/1975 | Clendinning et al. | 424/22 |
| 4,148,871 | 4/1979 | Pitt et al. | 424/22 |
| 4,264,574 | 4/1981 | Cherqui et al. | 424/19 |

FOREIGN PATENT DOCUMENTS

| | | |
|---|---|---|
| 1490855 | 6/1967 | France . |
| 2363251 | 3/1978 | France . |
| 2377431 | 8/1978 | France . |

OTHER PUBLICATIONS

Chemical Abstracts, vol. 92, No. 16, Apr. 21, 1980, abstract 92: 135249h.

*Primary Examiner*—Ronald W. Griffin
*Attorney, Agent, or Firm*—Weingarten, Schurgin, Gagnebin & Hayes

[57] ABSTRACT

The present invention relates to a new inert matrix having adjustable porosity and hardness.

This matrix comprises polycaprolactone having an average molecular weight of between 2000 and 70,000, which is in the form of agglomerated grains having an average diameter of between 50 and 500 $\mu$m and has a degree of crystallinity of at least 75%. The invention relates to the method for the preparation of a porous galenic form by means of the said matrix.

18 Claims, 4 Drawing Figures

INERT MATRIX BASED ON POLYCAPROLACTONE FOR THE ORAL ADMINISTRATION OF A DRUG, AND METHOD FOR THE PREPARATION OF THE GALENIC FORM COMPRISING THIS MATRIX

The present invention relates to a new physiologically inert matrix for the oral administration of a drug. This new matrix comprises a polymeric substance: polycaprolactone (abbreviated to "PCL" hereafter) as the essential ingredient. The invention also relates to the method for the preparation of the galenic form of controlled hardness and porosity, comprising this matrix.

It is known that substances such as cellulose derivatives, acrylic copolymers and PVC have been used in the field of pharmacology to prepare physiologically inert matrices. Now, it so happens that these substances, which are suitable for granulation by a wet process, are not all suitable for granulation by a dry process. Thus, of these substances, only cellulose derivatives, and in particular ethylcellulose, can be granulated by a dry process and compressed, but they give matrices which have the disadvantage of swelling again after compression, which are too friable and whose porosity cannot be adjusted according to the active principle incorporated. Furthermore, ethylcellulose, acrylic copolymers and PVC have the disadvantage of restricting the proportion of drug to a value of less than 40% by weight relative to the weight of the medicinal preparation containing the matrix, the drug and the other galenic adjuvants (especially a lubricant and a flow promoter).

Other sources, especially the articles by C. G. PITT et al., on the one hand J. Biomed. Mater. Res., 13, pages 497–507 (1979), and on the other hand J. Pharm. Sci., 68 (no. 12), pages 1534–1538 (1979), have disclosed the use of PCL films for preparing subcutaneous implants enabling a drug to be released over a period of time [3 to 12 months or more according to the first article by C. G. PITT et al. (cf. page 498, line 4); 2 to 14 months (theoretical calculation) or 20 to 200 days or more (in vitro and in vivo measurements) according to the second article by C. G. PITT et al. (cf. Table I and pages 1537–1538)].

These films capable of being used for implantation, which can (i) contain the drug in their bulk, (ii) be presented in the form of superimposed layers constituting laminates or sandwiches, or (iii), after having been rolled up or folded over onto themselves and sealed, serve as flexible envelopes or bags (capsules or sachets) containing the drug in their internal cavity, are not suitable for oral administration since the drug cannot be released during the normal gastrointestinal transit time and since a so-called "aqueous barrier layer" phenomenon, emphasized by PITT et al., can occur and restrict the release.

According to the invention, a new technical solution to the galenic problem of dry granulation is put forward, which makes it possible to overcome the above-mentioned disadvantages, especially those associated with cellulose derivatives, acrylic copolymers and PVC, and which offers the advantage of (i) making it possible to prepare, in particular, tablets which do not swell again after compression, are non-friable, are plastic (i.e. capable of absorbing shocks without breaking), have a porous and coherent structure and contain up to 80% by weight of drug, and (ii) controlling, without degradation of the active principle, the porosity and hardness of the medicinal preparations containing the drug, the PCL and the other adjuvants, in order to regulate the time-release. This technical solution, which uses PCL grains, also differs from the technique involving implantation by means of PCL films: after administration, the active principle or principles are released, during gastrointestinal transit, through the interstices present between the PCL grains, whereas they diffuse through the pores of the PCL films at a much slower rate.

The object of the invention is to propose a new matrix for the oral administration of a drug in the form of tablets of controlled porosity and hardness.

According to the invention, the term "active principle" is understood as meaning any therapeutically active and effective substance, the term "drug" is understood as meaning the said active principle or any mixture of at least two active principles, and the term "medicinal preparation" is understood as meaning any composition containing a drug in association with a physiologically acceptable excipient, i.e., in the case in point, the inert matrix and the other adjuvants such as, in particular, the lubricant and the flow promoter.

The term "inert matrix" is understood here as meaning that the matrix is not digested in the organism and that it does not have any interaction with the active principles or the fluids in the organism.

In the inert matrix, according to the invention, for the oral administration of a drug, which matrix comprises polycaprolactone, the polycaprolactone which it contains has an average molecular weight of between about 2000 and about 70,000, is in the form of grains having an average diameter of between 50 and 500 $\mu$m and has a degree of crystallinity of at least 75%.

The PCL according to the invention is a poly($\epsilon$-caprolactone) of the formula $+(CH_2)_5-CO-O+_n$, in which n is a number approximately equal to (i) 17 for an average molecular weight of 2000 and (ii) 615 for an average molecular weight of 70,000. Advantageously, the average molecular weight of the PCL will be between 30,000 and 45,000 and the degree of crystallinity will be between 80 and 95%.

To adjust the porosity and hardness of the matrix, the procedure used involves compression and then, if necessary, a treatment chosen from (i) heat treatment at a temperature of between 45° and 70° C. for a period less than or equal to 20 minutes, and (ii) treatment with a UHF (ultra-high frequency) field of about 1 MHz to about 25 GHz for a period less than or equal to 60 seconds and especially of between 10 and 60 seconds.

Compression makes it possible to effect agglomeration of the grains of the matrix with one another and/or with the drug and the other adjuvants, and consequently cohesion of the final product, and to ensure a measure of porosity in accordance with the compression force. This compression is advantageously carried out under a pressure greater than or equal to 100 daN/cm$^2$ (i.e. 10$^5$ pascals) and preferably of between 200 daN/cm$^2$ and 2000 daN/cm$^2$ (i.e. from 2×10$^5$ pascals to 2×10$^6$ pascals).

Calibration of the porosity can be adjusted according to the heat treatment or UHF treatment mentioned above, the latter advantageously being used to obtain medicinal preparations comprising an active principle sensitive to temperatures above 70° C. Heat treatment preferentially imparts surface hardness whereas UHF treatment preferentially imparts hardness to the bulk of the matrix. The heat treatment or UHF treatment gives a matrix whose porosity is such that the average diameter of the pores made up of the interstices present between the PCL grains is between 100 μm and 0.002 μm for a PCL particle size of between 500 μm and 50 μm.

The method for the preparation of a porous galenic form for oral administration, comprising a drug, a PCL matrix and other adjuvants, such as, in particular, the lubricant and flow promoter, successively comprises:

(a) granulating a mixture comprising the PCL having an average molecular weight of 2000 to 70,000, the drug, the lubricant, the flow promoter and, if appropriate, other adjuvants, to give a powder whose grains have a diameter of between 50 and 500 μm, (b) compressing all the components of the medicinal preparation under a pressure of 100 daN/cm$^2$ to 2000 daN/cm$^2$, and then, if appropriate, (c) carrying out a treatment chosen from the group consisting of (i) heat treatment at a temperature of between 45° and 70° C. for a period less than or equal to 20 minutes, and (ii) treatment with a UHF (ultrahigh frequency) field of about 1 MHz to about 25 GHz for a period less than or equal to 60 seconds and especially of between 10 and 60 seconds.

According to the invention, it is possible to obtain medicinal preparations in the form of tablets which can contain up to 80% by weight of drug.

In addition to the PCL and the drug, these tablets comprise one or more adjuvants conventionally used in pharmacology, in particular a lubricant (especially sodium stearate, magnesium stearate or potassium stearate), a flow promoter (especially colloidal silica), a flavor and/or a colorant.

Advantageously, 0.1 to 2% by weight of a lubricant, relative to the total weight of the medicinal preparation, and preferably 0.5% by weight of the said lubricant, will be used.

Likewise, 0.1 to 2% by weight (preferably 0.5% by weight) of flow promoter, relative to the total weight of the medicinal preparation, will be used.

Further advantages and characteristics of the invention will be understood more clearly on reading the following description of preparation examples, which in no way imply a limitation but are given by way of illustration.

PREPARATION I

A mixture having a particle size of 125–200 μm and comprising:

89% by weight of PCL having the following characteristics:
 formula: $+(CH_2)_5-CO-O+_n$
 n: 350 (average value)
 softening point: 58° C.
specific gravity: 0.2
 molecular weight: 40,000 (approximately)
 particle size: 125 to 200 μm
 degree of crystallinity: 86%,
10% by weight of KCl,
0.5% by weight of magnesium stearate and
0.5% by weight of colloidal silica
is granulated.

Tablets having a diameter of 12 mm and each weighing 350 mg are prepared from this mixture (on a KORSH alternating tablet compressing machine) by compression at 300 daN/cm$^2$.

The tablets thus obtained are then subjected to a heat treatment in an oven at 68° C., the duration of the said treatment being varied so that the influence of the said duration on the hardness of the tablets can be studied.

The results obtained made it possible to plot the curve of FIG. 1, in which the hardness (on the ordinate), expressed in kg, is given as a function of the duration of the heat treatment (on the abscissa), expressed in minutes. It is observed that (i) the matrices neither break nor shatter and (ii) in the case in point, a 15-minute heat treatment is sufficient to obtain the maximum hardness.

PREPARATION II

A mixture having a particle size of 125–200 μm and comprising:
49% by weight of the PCL of Preparation I,
50% by weight of KCl,
0.5% by weight of magnesium stearate and
0.5% by weight of colloidal silica
is granulated dry.

Tablets having a diameter of 12 mm and weighing 350 mg are prepared from the mixture granulated in this way, by compression at 300 daN/cm$^2$.

The tablets obtained are subjected to a heat treatment in an oven at 68° C., the duration of the said treatment being varied so that the kinetics of the release of the KCl can be studied.

Figure 2:
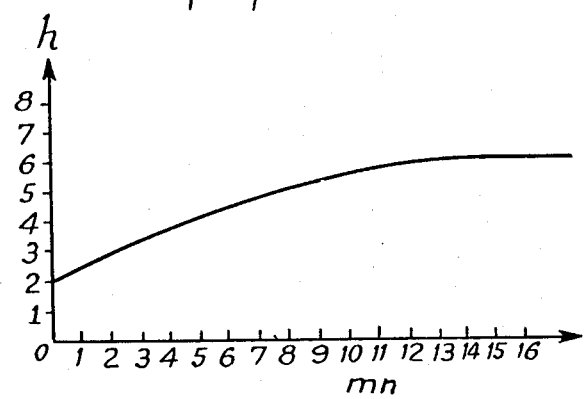

The results obtained made it possible to plot the curve of FIG. 2, in which the duration of release of KCl (on the ordinate), expressed in hours, is given as a function of the duration of the heat treatment (on the abscissa), expressed in minutes. It is observed that the duration of release of KCl follows HIGUCHI's law and that the maximum duration of release is reached after a heat treatment of 14 minutes. In the case in point, the heat treatment increases the duration of release by a factor of 3.

PREPARATION III

A powder of PCL having the following characteristics:
 n: 300 (average value)
 specific gravity: 0.2
 molecular weight: 36,000 (approximately)
 particle size: 100 to 400 μm
 degree of crystallinity: 93%
was used to prepare tablets (of diameter 12 mm and weight 350 mg) containing KCl, according to the operating procedures described in Preparation II, the heat treatment at 68° C. being replaced with a UHF treatment (frequency: 2450 MHz; power: 100 W) and the duration of the said UHF treatment being varied. The influence of the duration of the treatment on the kinetics of the release of KCl was studied and the corresponding results are collated in Table I.

TABLE I

| Influence of the duration of the UHF treatment on the duration of release of 50% by weight of the KCL contained in the tablets according to Preparation III | |
|---|---|
| Duration of treatment (in seconds) | Duration of release of 50% of the KCl (in hours) |
| 0 | 2 |
| 15 | 3 |
| 30 | 4 |
| 45 | 5 |
| 60 | 5 |

Figure 3:
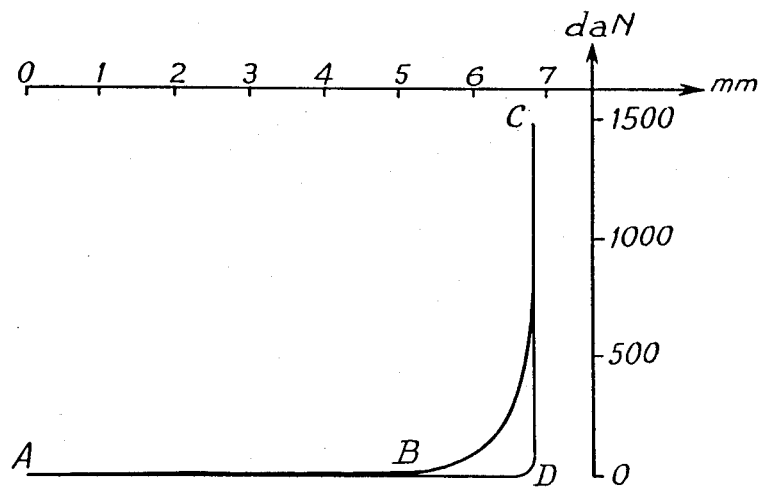

When preparing the tablets according to Preparation III, the compression cycle was studied and the results obtained made it possible to plot the curve of FIG. 3.

This compression cycle, represented by the displacement of the upper die (on the abscissa), expressed in mm, and the compression force (on the ordinate), expressed in daN, shows a packing period AB, a compression period BC and an ejection period CDA. By comparison with the compression cycle for conventional tablets, it is observed that the packing period is very long and that there is no seizing. It is also observed that the matrices of the tablets according to the invention have a high plasticity and that they retain their geometrical characteristics where the conventional tablets generally swell after ejection.

Figure 4:
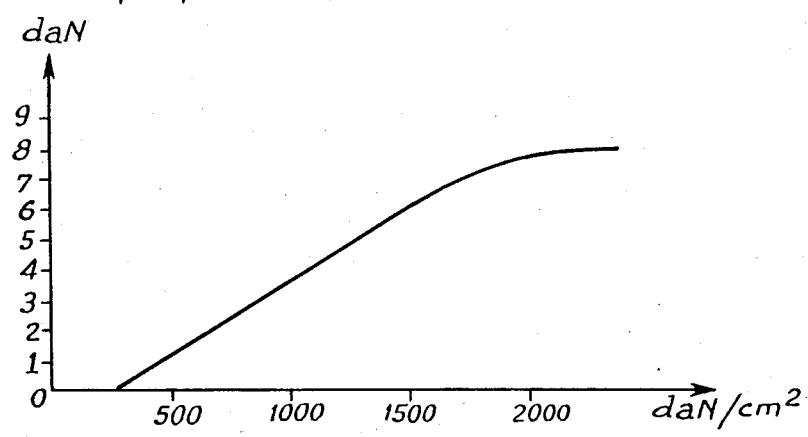

The same tablets were also used to study the influence of the compression force on the hardness of the matrix. The results obtained are represented by the curve of FIG. 4, in which the hardness (on the ordinate), expressed in daN, is given as a function of the compression force (on the abscissa), expressed in $daN/cm^2$. It was observed in the course of this study that the tablets do not break but are only deformed under the influence of compression.

PREPARATION IV

A mixture having a particle size of 50–500 μm and containing:
- 10, 20 or 40% by weight of verapamil,
- 0.5% by weight of magnesium stearate,
- 0.5% by weight of colloidal silica and
- 89, 79 or 59% by weight of PCL having the following characteristics:
  - n: 400 (average value)
  - softening point: 60° C.
  - specific gravity: 0.2
  - molecular weight: 45,000 (approximately)
  - particle size: 50–500 μm
  - degree of crystallinity: 91% is granulated dry.

The mixture granulated in this way is used to prepare tablets having a diameter of 12 mm and a thickness of between 3.2 and 3.5 mm (on a KORSH alternating tablet compressing machine), by compression at 1500 $daN/cm^2$.

The tablets containing 40% by weight of verapamil were then subjected to a heat treatment in an oven at 60° C. for 10, 15 or 20 minutes.

The duration of release of half of the quantity of verapamil contained in each type of tablet ($T_{\frac{1}{2}}$) was then measured. The results of this kinetic study have been collated in Table II.

TABLE II

Kinetic study of the release of 50% by weight of the verapamil contained in the tablets according to preparation IV

| Proportion of verapamil (% by weight) | Duration of the heat treatment (minutes) | Duration of release of half of the quantity of verapamil (minutes) |
| --- | --- | --- |
| 10% | 0 | 350 |
| 20% | 0 | 240 |
| 40% | 0 | 110 |
| 40% | 10 | 185 |
| 40% | 15 | 260 |
| 40% | 20 | 310 |

The results in Table II show how the time-release of the active principle is regulated according to the invention.

PREPARATION V

Tablets containing:
- 19% by weight of PCL,
- 80% by weight of fenofibrate,
- 0.5% by weight of magnesium stearate and
- 0.5% by weight of colloidal silica are prepared in accordance with the operating procedures described in Preparation IV, using the PCL of the said Preparation IV.

The kinetic study of the release of the fenofibrate {systematic nomenclature: isopropyl 2-[4-(4-chlorobenzoyl)phenoxy]-2-methylpropionate} shows that the time-release of the active principle can be controlled in vivo.

PREPARATION VI

Controlled-release tablets containing:
- 60% by weight of 2-[4-(4-chlorobenzoyl)phenoxy]-2-methylpropionic acid,
- 39% by weight of the PCL of Preparation III,
- 0.5% by weight of magnesium stearate and
- 0.5% by weight of colloidal silica are prepared in accordance with the operating procedures of Preparation III.

PREPARATION VII

Tablets containing:
- 59% by weight of 2-[4-(4-chloro-α-hydroxybenzyl)-phenoxy]-2-methylpropionic acid,
- 40% by weight of PCL,
- 0.5% by weight of magnesium stearate and
- 0.5% by weight of colloidal silica are prepared in accordance with the operating procedures of Preparation IV.

What is claimed is:

1. An inert polycaprolactone matrix for the oral administration of a drug, in which matrix, which has adjustable porosity and hardness, the polycaprolactone which it contains has a molecular weight of between about 2000 and 70,000, is in the form of agglomerated grains having an average diameter of between 50 and 500 μm and has a degree of crystallinity of at least 75%.

2. The matrix as claimed in claim 1, which has been subjected to compression under a pressure greater than or equal to 100 $daN/cm^2$.

3. The matrix as claimed in claim 1, which has been subjected to compression under a pressure of between 200 and 2000 $daN/cm^2$.

4. The matrix as claimed in claim 1, wherein the polycaprolactone which it contains has an average molecular weight of between 30,000 and 45,000.

5. The matrix as claimed in claim 1, wherein the average diameter of the pores made up of the interstices present between the polycaprolactone grains is between 0.002 μm and 100 μm.

6. The matrix as claimed in claim 1, wherein the polycaprolactone has a degree of crystallinity of between 80 and 95%.

7. The matrix as claimed in claim 1, which has been subjected to a heat treatment at a temperature of between 45° and 70° C. for a period less than or equal to 20 minutes.

8. The matrix as claimed in claim 1, which has been subjected to treatment with an ultra-high frequency field of about 1 MHz to about 25 GHz for a period less than or equal to 60 seconds.

9. The matrix as claimed in claim 8, wherein the treatment is carried out for a period of between 10 and 60 seconds.

10. A method for the preparation of a porous galenic form for oral administration by means of a polycaprolactone matrix as claimed in claim 1 which comprises:
   (a) granulating a mixture comprising the caprolactone having an average molecular weight of 2,000 to 70,000, the drug, a lubricant, and a flow promoter; and
   (b) subjecting the resulting mixture to compression under a pressure of 100 to 2000 daN/cm$^2$.

11. The method as claimed in claim 10, wherein the proportion of drug in the mixture of stage (a) is less than or equal to 80% by weight relative to the weight of the said mixture.

12. The method as claimed in claim 10, wherein the proportion of lubricant in the mixture of stage (a) is between 0.1 and 2% by weight relative to the weight of said mixture.

13. The method as claimed in claim 10, wherein the proportion of flow promoter in the mixture of stage (a) is between 0.1 and 2% by weight relative to the weight of said mixture.

14. The method as claimed in claim 13, wherein the proportion of lubricant in the mixture of stage (a) is about 0.5% by weight.

15. The method as claimed in claim 13, wherein the proportion of flow promoter in the mixture of stage (a) is about 0.5% by weight relative to the weight of said mixture.

16. A method for the preparation of a porous galenic form for oral administration by means of a polycaprolactone matrix as claimed in claim 1 which comprises:
   (a) granulating a mixture comprising the polycaprolactone having an average molecular weight of 2,000 to 70,000, the drug, a lubricant, and a flow promoter;
   (b) subjecting the resulting mixture to compression under a pressure of 100 to 2000 daN/cm$^2$; and
   (c) subjecting the resulting tablets to a heat treatment at a temperature of between 45° and 70° C. for a period less than or equal to 20 minutes.

17. A method for the preparation of a porous galenic form for oral administration by means of a polycaprolactone matrix as claimed in claim 1 which comprises:
   (a) granulating a mixture comprising the polycaprolactone having an average molecular weight of 2,000 to 70,000, the drug, a lubricant, and a flow promoter;
   (b) subjecting the resulting mixture to compression under a pressure of 100 to 2000 daN/cm$^2$; and
   (c) subjecting the resulting tablets to treatment with an ultra-high frequency field of about 1 MHz to about 25 GHz for a period of less than or equal to 60 seconds.

18. The method according to claim 17, wherein the treatment with an ultra-high frequency field is carried out for a period of between 10 and 60 seconds.

* * * * *